United States Patent [19]

Medwid et al.

[11] Patent Number: 4,692,449

[45] Date of Patent: Sep. 8, 1987

[54] SUBSTITUTED QUINOLINEDIONES

[75] Inventors: Jeffrey B. Medwid, West Nyack; Lawrence W. Torley, Washingtonville, both of N.Y.

[73] Assignee: American Cyanamid Company, Stamford, Conn.

[21] Appl. No.: 876,600

[22] Filed: Jun. 20, 1986

[51] Int. Cl.$^4$ .................. A61K 31/495; C07D 401/04
[52] U.S. Cl. .................................... 514/254; 544/295; 544/353; 544/354; 544/363; 546/179
[58] Field of Search ...................... 544/363, 254, 295

[56] References Cited

U.S. PATENT DOCUMENTS 3,994,900 11/1976 Krapcho et al. .................... 544/363

Primary Examiner—Glennon H. Hollrah
Assistant Examiner—James H. Turnipseed
Attorney, Agent, or Firm—Edward A. Conroy, Jr.

[57] ABSTRACT

This disclosure describes novel 6-(4-substituted-1-piperazinyl)-5,8-quinolinediones, 7-(4-substituted-1-piperazinyl)-5,8-quinolinediones, and 6-(4-substituted-1-piperazinyl)-5,8-quinoxalinediones which possess activity an anti-asthmatic and anti-allergic agents.

10 Claims, No Drawings

SUBSTITUTED QUINOLINEDIONES

BRIEF SUMMARY OF THE INVENTION

This invention relates to new organic compounds and, more particularly, is concerned with novel substituted quinolinediones and quinoxalinediones which may be represented by the following structural formula:

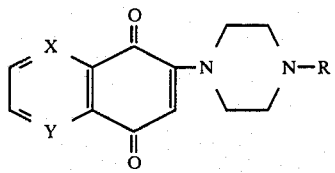

wherein X is methylidyne (=CH—) or nitrilo (=N—) and Y is methylidyne (=CH—) or nitrilo (=N—) with the proviso that at least one of X and Y is nitrilo (=N—), and R is alkyl($C_1$-$C_3$), carboalkoxy($C_2$-$C_4$), alkanoyl($C_1$-$C_3$), phenyl, benzyl, m-trifluoromethylphenyl, 2-pyridyl, 2-pyrimidyl, 2-benzoxazolyl or 2-benzothiazolyl.

The organic bases of this invention form non-toxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, maleic, lactic, malic, succinic, tartaric, acetic, fumaric, gluconic, ascorbic, and the like. For purposes of this invention the free bases are equivalent to their non-toxic acid-addition salts. The acid-addition salts of the organic bases of the present invention are, in general, crystalline solids, relatively soluble in water, methanol and ethanol but relatively insoluble in non-polar organic solvents such as diethyl ether, benzene, toluene, and the like.

DETAILED DESCRIPTION OF THE INVENTION

The novel substituted quinoxalinediones of the present invention may be readily prepared as set forth in the following reaction scheme wherein R is as hereinbefore defined:

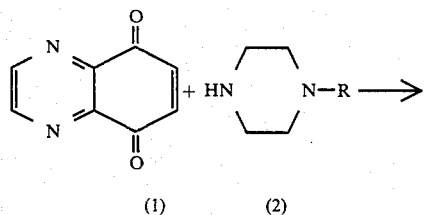

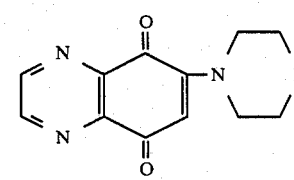

In accordance with the above reaction scheme, 5,8-quinoxalinedione (1) is reacted with an appropriately substituted piperazine (2) in an inert solvent such as dioxane, dimethylformamide or tetrahydrofuran at ambient temperatures for about 2-5 hours to provide the final product (3).

The novel substituted quinolinediones of the present invention may be readily prepared as set forth in the following reaction scheme wherein R is as hereinbefore defined:

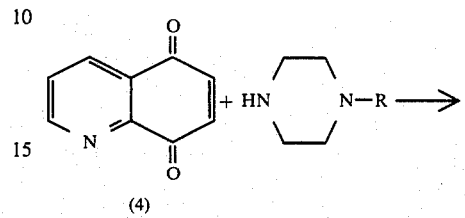

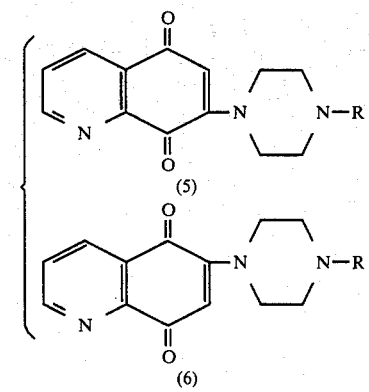

In accordance with the above reaction scheme, 5,8-quinolinedione (4) is reacted with an appropriately substituted piperazine (2) in an inert solvent such as 1,2-dimethoxyethane, dioxane or tetrahydrofuran at ambient temperatures for about 4-48 hours to provide a mixture of the 7-isomer (5) and the 6-isomer (6).

The novel compounds of the present invention are highly active as antiasthmatic and antiallergic agents as will be demonstrated hereinbelow.

The bronchospasm of allergic asthma is a consequence of the release of mediators, such as histamine and slow-reacting substances from mast cells. The role of mediator release in the induction of an asthmatic attack has been fully reviewed and documented, see Kaliner, M. and Austen, K. F., Bronchial Asthma Mechanisms and Therapeutics, E. B. Weiss, Editor, Little, Brown and Company, Boston, 163 (1976); Lichtenstein, L. M., Asthma-physiology, Immunopharmacology and Treatment, Second International Symposium, L. M. Lichtenstein, and K. F. Austen, Editors, Academic Press, New York, 51 (1979); and Bell, S. C., ed al., Annual Reports in Medicinal Chemistry, 14, 51, H. J. Hess, Editor, Academic Press, New York (1979).

The novel compounds of this invention have been tested by the procedure of Lichtenstein, L. M. and Osler, A. G., J. Exp. Med., 120, 507-530 (1964), which evaluated the ability of compounds to inhibit mediator (histamine) release from immunologically stimulated human basophils.

REAGENTS

10X Concentrated Tris Buffer

Dissolve 140.3 g of sodium chloride, 7.45 g of potassium chloride and 74.5 g of Trizma-Tris Pre-Set, Reagent Grade, pH 7.6, at 25° C. (Sigma Chemical Co.) in sufficient water to give a final volume of 2 liters.

Human Albumin (Sigma Chemical Co.) (30 mg/ml)

Calcium and Magnesium Stocks

Made to 0.75M and 0.5M respectively, with calcium chloride dihydrate and magnesium chloride hexahydrate.

Tris-A Buffer

A 10 ml portion of 10X Tris Buffer and 1.0 ml of human albumin are diluted to 100 ml with water.

Tris ACM Buffer

A 10 ml portion of 10X Tris Buffer, 1.0 ml of human albumin, 0.8 ml of calcium stock and 0.2 ml of magnesium stock are diluted to 100 ml with water.

Rabbit Antihuman IgE

Behring Diagnostics (Generally used at 10 g protein/ml final concentration).

House Dust Mite Extract (*Dermatophagoides Farinae*)

Strength 1:100 (w:v) allergenic extract, Hollister-Stier Labs. Generally this is diluted 1:1000 to 1:10,000 (considering the vial as stock).

Other Allergens

Intradermal solutions of intramuscular preparations for hyposensitization, Hollister-Stier Labs. The final concentration used is on the order of 1 PNU/ml.

Separation of Leukocytes from Human Blood and Challenge

Eighty milliliters of blood is withdrawn from subjects with known histamine release to anti-IgE, ragweed antigen or other specific allergen, using four 20 ml heparinized tubes. This 80 ml of blood is mixed with 20 ml of saline containing 0.6 g of dextrose and 1.2 g of dextran. The blood is allowed to sediment at room temperature in two 50 ml polycarbonate centrifuge tubes until a sharp interface develops between the red cells and plasma (60–90 minutes). The plasma (top) layer from each tube is withdrawn by pipet and transferred to respective 50 ml polycarbonate tubes. The plasma is centrifuged for 8 minutes at $110 \times G$ at 4° C. The supernatant is carefully poured off as completely as possible and the cell button is resuspended in 2–3 ml of Tris-A buffer using a silconized Pasteur pipet. The resuspension is accomplished by drawing the liquid gently in an out of the pipet, with the tip below the liquid, until and even suspension of cells is obtained. Sufficient Tris-A buffer is then added to bring the volume in the tube to about 45 ml and the tube is centrifuged at $110 \times G$ for 8 minutes at 4° C. The supernatant is poured off and the cell button is resuspended and centrifuged as described above. The supernatant is poured off and the cell button suspended in 2–3 ml of Tris-ACM buffer to make the final volume sufficient to allow addition to the reaction tubes.

Reaction tubes containing anti-IgE or antigens, either alone or with test compound in a total volume of 0.2 ml are prepared and placed in a 37° C. bath. The cells are warmed to 37° C. and frequently swirled to ensure and even suspension, while 1.0 ml aliquots are added to each reaction tube. The tubes are then incubated for 60 minutes at 37° C., vortexing the tubes gently every 15 minutes to keep the cells evenly suspended. When the reaction is complete, the tubes are centrifuged at 4° C. for 10 minutes at 1500 rpm to sediment the cells. one ml aliquots of supernatant are transferred to 12 mm by 75 mm polyethylene tubes and 0.2 ml of 8% perchloric acid is added to each tube. Blanks and totals are included in each test. The blanks have cells and all reagents except antigent or anti-IgE. The totals contain 0.24 ml of 8% perchloric acid, one ml of cells and 0.2 ml of buffer. All samples are then centrifuged to remove the precipitate protein.

Assay of Released Histamine by the Automated Fluorometric Method

This automated method has been described by Siraganian, R. P., in Anal. Biochem., 57 383 (1974) and J. Immunol. Methods, 7 283 (1975) and is based on the manual method of Shore, P. A., et al., J. Pharmacol. Exp. Ther., 217, 182 (1959).

The automated system consists of the following Technicon Autoanalyzer II components: Sampler IV, Dual-Speed Proportioning Pump III, Fluoronephelometer with a narrow pass primary filter 7–60 and a secondary filter 3–74, Recorder, and Digital Printer. The manifold used is the one described by Siraganian vide supra, with the following modifications: the dialyzer is omitted; all pumping tubes pass through a single proportioning pump with large capacity and twice the volume of sample is taken for analysis.

The automated chemistry consists of the following steps: Extraction from alkaline saline into butanol, back extraction into dilute hydrochloric acid by addition of heptane, reaction of histamine with o-phthaldialdehyde (OPT) at high pH and conversion of the OPT adduct to a stable fluorophore with phosphoric acid. The reaction product is then passed through the fluorometer. The full scale response is adjusted to 50 ng histamine based with a threshold sensitivity of approximately 0.5 ng.

Calculation of the Results of Histamine Release Tests

The instrument blank (wash) is substracted from the ng histamine of each sample. Then the ng histamine of each sample is divided by the mean of the three totals (cells lysed with perchloric acid) to obtain percent release.

Control samples contain antigen but no test compound. Blank (or spontaneous release) samples contain neither antigen nor test compound. The mean of the blanks (three replicates) is subtracted from the percent release for controls and test compounds.

The means for control and tests compound groups are computed and the results for a test compound is computed as percent of control by the formula:

$$100 \times \frac{\% \text{ Histamine Release with Test Compound}}{\% \text{ Histamine Release in Controls}}$$

Values obtained at different concentrations of test compound are used to calculate an $ED_{50}$ (the concentration in $\mu M$ which causes a 50% inhibition of histamine release) by linear regression. A compound is considered active if the $ED_{50}$ is $\leq 48$ $\mu M$.

The results of this test on typical compounds of this invention appear in Table I.

TABLE I

Inhibition of Histamine Release from Immunologically Stimulated Human Basophils

| Compound | $ED_{50}\mu M$ |
| --- | --- |
| 4-(5,8-Dihydro-5,8-dioxo-6-quinoxalinyl)-1-piperazinecarboxylic acid, ethyl ester | 3.7 |
| 6-[4-[3-(Trifluoromethyl)phenyl]-1-piperazinyl]5,8-quinoxalinedione | 6.6 |
| 6-[4-(2-Benzothiazolyl)-1-piperazinyl]-5,8-quinoxalinedione | 1.2 |
| 4-(5,8-Dihydro-5,8-dioxo-6-quinolinyl)-1-piperazinecarboxylic acid, ethyl ester | 17.4 |
| 6-[4-(phenylmethyl)-1-piperazinyl]-5,8-quinolinedione | 12.1 |

The ability of these compounds to inhibit lipoxygenase activity in terms of the suppression of the release and biosynthesis of leukotriene B4 (LTB4) and 5-hydroxyeicosatetraenoic acid (5-HETE) was measured as follows.

In this assay $3 \times 10^7$ peritoneal neutrophils derived from guinea pigs were incubated at 37° C. in Dulbeccos buffer containing 50 mM tris buffer (pH 7.4). Five minutes before the addition of 100 μM arachidonic acid and 20 μM calcium ionophore (A23187), control vehicle or the test compounds were added to the neutrophils at a concentration of 10 μg/ml.

Three minutes after the addition of arachidonic acid and calcium ionophore the total lipid was partitioned into chloroform after adjusting the pH to 3 with citric acid and the addition of equal parts of methanol and chloroform.

The 5-HETE and LTB4 were resolved by HPLC using a 5M, 4×25 cm octadecyl silica column (IBM Instruments) with 70–80% methanol in water adjusted to pH 3.0 with acetic acid. As the mobile phase was pumped at 1.0 ml/minute, LTB4 and 5-HETE were detected by absorbance at 270 and 236 nm, respectively.

LTB4 and 5-HETE were quantitated by comparison with the control and the results were expressed as a percent of control. The lower the percentage, the more active the compound.

The results of this test on representative compounds of the invention appear in Table II.

TABLE II

Inhibition of Neutophil Lipoxygenase from Immunologically Stimulated Guinea Pig Neutrophiles

| Compound | % of Control LTB4 | 5-HETE |
| --- | --- | --- |
| 6-[4-[3-(Trifluoromethyl)phenyl]-1-piperazinyl]-5,8-quinoxalinedione | 0 | 1.6 |
| 6-[4-(Phenylmethyl)-1-piperazinyl]-5,8-quinoxalinedione | 8 | 53.9 |
| 6-[4-(2-Benzothiazolyl)-1-piperazinyl]5,8-quinoxalinedione | 8 | 67.2 |
| 6-[4-[3-Trifluoromethyl)phenyl]-1-piperazinyl]-5,8-quinolinedione | 5.7 | 11.9 |
| 6-[4-(2-Benzoxazolyl)-1-piperazinyl]-5,8-quinolinedione | 8 | 36.9 |
| 7-[4-(2-Benzoxazolyl)-1-piperazinyl]-5,8-quinolinedione | 35.8 | 22.7 |

The novel compounds of the present invention are effective as antiasthmatic agents in mammals when administered in amounts ranging from about 0.1 mg to about 10 mg/kg of body weight per day. A preferred dosage regimen for optimum results would be from about 0.1 mg to about 25 mg/kg of body weight per day, and such dosage units are employed that a total of from about 7 mg to about 1.8 g of the active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, aerosol, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafter and the like. Such compositions and preparation should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phophate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capusles may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In additional, these active compounds may be incorporated into sustained-release preparations and formulations.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a ;mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned nonvolatile polyethylene glycols may be employed, it is preferred to use a mixture having an average molecular weight of from about 200 to about 400.

In addition to the active compound, the partenteral solutions may contain various preservatives which may be used to prevent bacterial and fungal contamination. Such preservatives are, for example, myristyl-gamma-picolinium chloride, benzalkonium chloride, phenethyl alcohol, p-chlorophenyl-alpha-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed. These compounds may also be administered by inhalation using conventional Aerosl(®) formulations.

The invention will be described in greater detail in conjunction with the following specific examples.

EXAMPLE 1

5,8-Quinoxalinedione

A 9.2 g portion of 5,8-dihydroxyquinoxaline in 300 ml of p-dioxane was heated at reflux with 16.2 g of silver oxide for 6 hours. The mixture was cooled, then filtered and the filtrate concentrated in vacuo. The residue was slurried with 75 ml of acetone, cooled and the solid collected, washed with acetone and dried, giving 8.0 g of the desired product, mp 172°–173° C.

EXAMPLE 2

4-(5,8-dihydro-5,8-dioxo-6-quinoxalinyl)-1-piperazine carboxylic acid ethyl ester A mixture of 160 mg of 5,8-quinoxalinedione and 316 mg of 1-piperazinecarboxylic acid ethyl ester in 10 ml of dioxane was stirred for 3 hours. The resulting solid was collected, washed with ether and dried, giving 150 mg of the desired product as a red solid, mp 180°–195° C. (dec.).

EXAMPLE 3

6-[4-[3-(Trifluoromethyl)phenyl]-1-piperazinyl]-5,8-quinoxalinedione

A mixture of 160 mg of 5,8-quinoxalinedione, 460 mg of 4-[3-(trifluoromethyl)phenyl]-1-piperazine in 10 ml of dioxane was stirred for 3 hours, then diluted with 20 ml of ether and stirred an additional hour. The solid was collected, giving 110 mg of the desired product as crystals, mp 165°–190° C. (dec.).

EXAMPLE 4

6[4-(Phenylmethyl)-1-piperazinyl]-5,8-quinoxalinedione

A mixture of 160 mg of 5,8-quinoxalinedione and 352 mg of 1-benzylpiperazine in 10 ml of dioxane was stirred or 3 hours. The solvent was then removed and the residue triturated with ether. This solid was collected, washed with ether and dried, giving 110 mg of the desired product, mp 165°–168° C. (dec.).

EXAMPLE 5

6-[4-(2-Benzothiazoyl)-1-piperazinyl]-5,8-quinoxalinedione

A mixture of 640 mg of 5,8-quinoxalinedione and 876 mg of 4-(2-benzothiazolyl)-1-piperazine in 40 ml of dioxane was stirred for 24 hours. The solid was collected, giving 650 mg of the desired product, mp 104°–105° C.

EXAMPLE 6

5,8-Quinolinedione

To a solution of 23.2 g of 5-hydroxyquinoline in 1600 ml of methanol in an ice bath was added a total of 36 g of potassium dihydrogen phosphate and 96 g of potassium nitroso disulfonate in 8.8 liters of water in five portions over a 1 hour period. The mixture was then stirred overnight at room temperature, followed by extraction with four 1500 ml portions of chloroform. The extracts were combined, dried, filtered through alumina and evaporated to dryness, giving 12.0 g of crude product. An analytical sample was prepared by crystallization from petroleum ether, mp 110° C.

EXAMPLE 7

6-[4-[3-(Trifluoromethyl)phenyl]-1-piperazinyl]-5,8-quinolinediones

A 1.1 g portion of 5,8-quinolinedione was dissolved in 100 ml of 1,2-dimethoxyethane. A solution of 3.45 g of 4-[3-(trifluoromethyl)phenyl]-1-piperazine in 25 ml of 1,2-dimethyoxyethane was added dropwise with stirring over 10 minutes. Stirring was continued for 30 minutes, then 1 g of silver oxide was added and stirring continued for 48 hours. The mixture was filtered and the filtrate evaporated. The residue was triturated with ethyl acetate and the solid collected. This solid was boiled in ethyl acetate, then cooled and the orange solid collected, giving 1.45 g of the desired product, mp 186°–188° C.

EXAMPLE 8

4-(5,8-Dihydro-5,8-dioxo-6-quinolyl)-1-piperazinecarboxylic acid ethyl ester

A mixture of 1.1 g of 5,8-quinolinedione in 100 ml of 1,2-dimethoxyethane was added dropwise to a solution of 2.37 g of 1-piperazinecarboxylic acid, ethyl ester in 25 ml of 1,2-dimethyoxyethane with stirring. Stirring was continued for 30 minutes, then 1 g of silver oxide was added and this mixture was stirred overnight. The mixture was filtered and the solid washed with dichloromethane. The filtrate and wash were combined, evaporated, triturated with ethyl acetate and the solid collected. This solid was chromatographed, eluting with dichloromethane, then ethyl acetate. The active fractions were combined and evaporated, giving 817 mg of the desired product, mp 192°–194° C. (dec.).

EXAMPLE 9

6-[4-(Phenylmethyl)-1-piperazinyl]-5,8-quinolinedione

To a solution of 1.1 g of 5,8-quinolinedione in 100 ml of 1,2-dimethoxyethane was added dropwise a solution of 2.64 g of 4-(phenylmethyl-1-piperazine in 25 ml of 1,2-dimethoxyethane during 10 minutes with stirring. Stirring was continued for 30 minutes, then 1 g of silver oxide was added, the mixture was stirred overnight and filtered. The filtrate was evaporated. The residue was triturated with ethyl acetate giving an orange solid. This solid was chromatographed on silica gel packed in dichloromethane and eluted with ethyl acetate. The minor component was isolated and saved (see Example 10). The major component was isolated and dried, giving 295 mg of the desired product, mp 167°–169° C. (dec.).

EXAMPLE 10

7-[4-(Phenylmethyl)-1-piperazinyl]-5,8-quinolinedione

The minor component isolated in Example 9 gave 83 mg of the desired product as identified by proton nuclear magnetic resonance.

EXAMPLE 11

6-[4-(2-Benzoxazolyl)-1-piperazinyl]-5,8-quinolinedione

To a solution of 1.1 g of 5,8-quinolinedione in 100 ml of 1,2-dimethoxyethane was added dropwise, with stirring over 10 minutes, 1.7 g of 4-(2-benzoxazolyl)-1-piperazine in 25 ml of 1,2-dimethoxyethane. Stirring was continued for 18.5 hours and the solid collected and saved. The filtrate was evaporated and the residue triturated with ethyl acetate. This solid was collected, combined with the above solid and chromatographed on silica gel eluting with dichloromethane, then ethyl acetate, and finally chloroform:methanol (20:1). The desired fractions were combined and evaporated, givng 1.35 g of the desired product, mp 200° C. (dec.).

The less polar compoent was treated as described in Example 12.

EXAMPLE 12

7-[4-(2-Benzoxazolyl)-1-piperazinyl]-5,8-quinolinedione

The less polar component, isolated in Example 11, was dried, giving 80 mg of the desired product, mp 235°–240° C. (dec.).

EXAMPLE 13

6-Chloro-5,8-quinolinediol, hydrochloride

A 5.0 g portion of 5,8-quinolinedione was dissolved in 450 ml of 1,2-dimethoxyethane and anhydrous hydrogen chloride was bubbled into the solution for 2.5 hours in an ice bath. The solid (3.58 g) was collected by filtration and both solid and filtrate was saved (see Example 14). A 100 mg portion of this solid was recrystallized from aqueous methanol, giving 60 mg of the desired product as a yellow solid.

EXAMPLE 14

6-Chloro-5,8-quinolinedione

The filtrate saved in Example 13 was dried overnight giving 1.86 g of solid which was combined with the 3.48 g of solid saved in Example 13. The combined solid was stirred in 250 ml of a saturated aqueous solution of sodium acetate for 2.5 hours. The resulting solid was collected, washed with water, then dichloromethane and dried. This solid was treated with a solution of 3.8 g of silver oxide in 1,2-dimethyoxyethane for 2.5 hours and then filtered. The filtrate was concentrated to 50 ml and then poured into 300 ml of petroleum ether. This suspension was treated with dichloromethane and the solid collected. This solid was boiled in dichloromethane and then chromatographed on silica gel, eluting with hot dichloromethane, then with dichloromethane:methanol (100:1). All the fractions were combined, evaporated and reoxidized with 1.5 g of silver oxide in 150 ml of 1,2-dimethoxyethane overnight. The mixture was filtered through diatomaceous earth, treated with activated charcoal, filtered through hydrous magnesium silcated and the filtrate evaporated. The residue was chromatographed on silica gel, eluting with dichloromethane. Fractions 1 and 2 were combined and evaporated, giving 90 mg of the desired product.

EXAMPLE 15

6-[[2-(2-Benzothiazolylmethylamino)ethyl]methylamino]-5,8-quinoxalinedione

To a slurry of 320 mg of 5,8-quinoxalinedione and 884 mg of N-2-benzothiazolyl-N-N'-dimethyl-1,2-ethanediamine in 25 ml of 1,2-dimethoxyethane was added 276 mg of silver oxide. The mixture was stirred 24 hours, diluted with 100 ml of dichloromethane and filtered. The filtrate was evaporated, the residue triturated with ether and the solid collected, giving 720 mg of the desired product.

We claim:

1. A compound selected from the group consisting of those of the formulae:

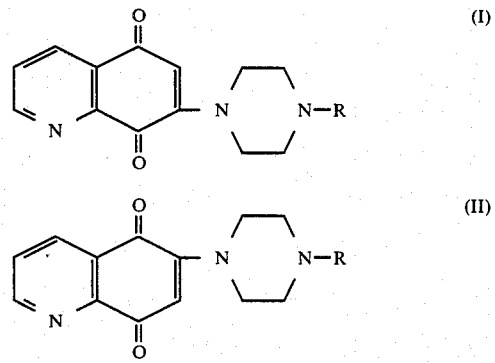

wherein R is alkyl($C_1$–$C_3$), carboalkoxy($C_2$–$C_4$), alkanoyl($C_1$–$C_3$), benzyl, phenyl, m-trifluoromethylphenyl, 2-pyridyl, 2-pyrimidyl, 2-benzoxazolyl or 2-benzothiazolyl and the pharmacologically acceptable acid-addition salts thereof.

2. The compound according to claim 1, formula (II) thereof; 6-[4-(3-trifluoromethylphenyl)-1-piperazinyl]-5,8-quinolinedione.

3. The compound according to claim 1, formula (II) thereof; 6-(4-carbethoxy-1-piperazinyl)-5,8-quinolinedione.

4. The compound according to claim 1, formula (II) thereof; 6-(4-benzyl-1-piperazinyl)-5,8-quinolinedione.

5. The compound according to claim 1, formula (I) thereof; 7-(4-benzyl-1-piperazinyl)-5,8-quinolinedione.

6. The compound according to claim 1, formula (II) thereof; 6-[4-(2-benzoxazolyl)-1-piperazinyl]-5,8-quinolinedione.

7. The compound according to claim 1, formula (I) thereof; 7-[4-(2-benzoxazolyl)-1-piperazinyl]-5,8-quinolinedione.

8. A method of treating asthma and allergic diseases in a mammal which comprises administering to said mammal an effective amount of a compound of claim 1.

9. A method of treating inflammation in a mammal which comprises administering to said mammal an effective amount of a compound of claim 1.

10. A composition of matter in dosage unit form comprising from about 5 mg to about 1500 mg of a compound of claim 1 in association with a pharmaceutically acceptable carrier.

* * * * *